(12) United States Patent
Krause et al.

(10) Patent No.: US 9,091,664 B2
(45) Date of Patent: Jul. 28, 2015

(54) PULSED EDDY CURRENT SENSOR FOR PRECISION MEASUREMENT AT-LARGE LIFT-OFFS ON METALLIC SURFACES

(76) Inventors: Thomas Krause, Kingston (CA);
Roderick J. McGregor, Victoria (CA);
Alexandr Tetervak, Kingston (CA);
Ross Underhill, Kingston (CA)

( * ) Notice: Subject to any disclaimer, the term of this patent is extended or adjusted under 35 U.S.C. 154(b) by 462 days.

(21) Appl. No.: 13/490,795

(22) Filed: Jun. 7, 2012

(65) Prior Publication Data
US 2013/0328555 A1    Dec. 12, 2013

(51) Int. Cl.
*G01N 27/90* (2006.01)

(52) U.S. Cl.
CPC .................................. *G01N 27/9053* (2013.01)

(58) Field of Classification Search
USPC ........................................................ 324/230
See application file for complete search history.

(56) References Cited

U.S. PATENT DOCUMENTS

| | | | | |
|---|---|---|---|---|
| 2,629,004 | A * | 2/1953 | Greenough | 369/146 |
| 3,848,183 | A | 11/1974 | Puidak | |
| 3,922,599 | A * | 11/1975 | Steingroever et al. | 324/230 |
| 3,940,689 | A | 2/1976 | Johnson, Jr. | |
| 4,523,147 | A | 6/1985 | D'Angelo et al. | |
| 5,068,608 | A | 11/1991 | Clark, Jr. | |
| 5,371,461 | A | 12/1994 | Hedengren | |
| 5,391,988 | A | 2/1995 | Kitagawa | |
| 5,506,503 | A | 4/1996 | Cecco et al. | |
| 5,617,024 | A * | 4/1997 | Simpson et al. | 324/209 |
| 5,886,522 | A * | 3/1999 | May | 324/230 |
| 6,486,673 | B1 | 11/2002 | Goldfine et al. | |
| 6,636,037 | B1 | 10/2003 | Ou-Yang | |
| 6,657,429 | B1 | 12/2003 | Goldfine et al. | |
| 7,560,920 | B1 | 7/2009 | Ouyang et al. | |
| 7,657,389 | B2 | 2/2010 | Suh et al. | |
| 7,994,781 | B2 | 8/2011 | Goldfine et al. | |
| 8,008,913 | B2 | 8/2011 | Qiao et al. | |
| 8,436,608 | B2 * | 5/2013 | Sun et al. | 324/240 |
| 8,717,012 | B2 * | 5/2014 | Wincheski et al. | 324/239 |
| 2002/0008511 | A1 * | 1/2002 | Davies | 324/230 |
| 2002/0093330 | A1 * | 7/2002 | Crouzen et al. | 324/240 |
| 2002/0149359 | A1 * | 10/2002 | Crouzen et al. | 324/229 |

(Continued)

FOREIGN PATENT DOCUMENTS

JP          61264251       11/1986
WO     WO 2009036989       3/2009

OTHER PUBLICATIONS

A novel method for surveying insulated ferrous components—Applus + RTD-NDT & Inspection—Incotest, available as of Jun. 6, 2012.

(Continued)

*Primary Examiner* — Jay Patidar
(74) *Attorney, Agent, or Firm* — Benoit & Cote Inc.

(57) ABSTRACT

There is described a pulsed eddy current sensor for measurement of a lift-off distance over a surface of a metallic substrate (a metallic surface). The pulsed eddy current sensor comprises: a primary excitation coil to which are applied voltage pulses for generating primary magnetic fields, wherein an interaction of the primary magnetic fields with the metallic substrate produces secondary magnetic fields; and secondary pick-up probes, each of the secondary pick-up probes located at a different vertical distance from the metallic surface, the secondary pick-up probes used for measuring the primary and secondary magnetic fields and for producing a differential signal that is representative of the lift-off distance.

12 Claims, 14 Drawing Sheets

(56) References Cited

U.S. PATENT DOCUMENTS

| | | | |
|---|---|---|---|
| 2003/0169035 A1* | 9/2003 | Crouzen | 324/230 |
| 2004/0066189 A1 | 4/2004 | Lopez | |
| 2004/0080316 A1 | 4/2004 | Friend et al. | |
| 2006/0202688 A1 | 9/2006 | Woods et al. | |

OTHER PUBLICATIONS

Tian et al., "Reduction of lift-off effects for pulsed eddy current NDT", Science d Direct—NDT & E International 38 (2005) 319-324—www.elsevier.com/kicate/ndteint.

Waters, "RTD—Incotest—For the dectection of corrosion under insulation", Manager-Advanced Inspection Services PNDT PTY Ltd, Perth Western Australia, available as of Jun. 6, 2012.

Yang et al. "Pulsed eddy-current measurement of a conducting coating on a magnetic metal plate", Tai-Intitute of Physics Publishing, Meas. Sci. Technol. 13 (2002) 1259-1265—Online at: stacks.lop.org/MST/13/1259.

\* cited by examiner

PULSED EDDY CURRENT SENSOR FOR PRECISION MEASUREMENT AT-LARGE LIFT-OFFS ON METALLIC SURFACES

BACKGROUND (a) Field

The subject matter disclosed generally relates to non-destructive testing (NDT). More particularly, the subject matter relates to NDT using pulsed eddy currents (PEC).

(b) Related Prior Art

Metallic surfaces of engineered systems such as, without limitations, aircraft systems, naval systems, nuclear systems, oil and gas systems, and the like, often require inspection of the surfaces for the purposes of, without limitations, precise geometric characterization, corrosion detection, crack detection, water ingress, coating delamination, impact damage assessment, and the like.

A range of non destructive inspection (NDI) technologies, including metrology instruments, are available in the industry for such measurements. However, the metal surface is frequently hidden by thin coatings such as paints applied for corrosion protection, or thick coatings applied for, without limitations, insulation, radar and/or sonar absorption, damage protection, aesthetics and the like. Thus, thick surface coatings block access to the metallic surfaces for metrology instruments requiring physical contact, and block the line-of-sight required for non-contacting instruments.

Typically, inspection of metal under thick coatings requires removal of the coating to expose the metal substrate as current technology cannot effectively execute a measurement with the coating in place. Such removal and replacement is costly and discourages or restricts thorough wide-area inspection.

In recent years, various new metrology technologies have matured to address the need for improved field deployability, simplicity and precision in the process of satisfying the geometric characterization needs of maintenance planners and engineering analysts. Systems using, without limitations, lasers, photogrammetric triangulation, and other principles are commercially available. Requiring either line-of-sight or physical contact with the measurement point, use of these systems to measure points on a surface beneath a thick coating can at best measure a coordinate on the coating above the actual point of interest.

Although various technologies are available for inspections when the metal surface is exposed by removal of the coating, no solution is commercially available for inspection through thick coatings for the surface topology measurements at high resolution.

For example, to provide stealth during operations, the bulk of the outside surface of submarines is covered with specially designed anechoic tiles. These tiles are engineered to absorb sound energy originating from inside the submarine and to damp reflections of sound generated by external sonar detection systems. Unfortunately, the presence of anechoic tiles obviously complicates inspections of the substrate structural hull, such as routine circularity checks and evaluation of hull surface condition. Random variations in thickness of the tile and applied adhesive epoxy layer preclude any prospect of extrapolation of the shape of the steel hull from the external shape of the tiled submarine to the required precision (i.e., within 1 mm).

Furthermore, occasional disbond of the tiles from the hull surface results in tile deformations, which further impact external measurements. Tiles may also conceal hull surface conditions arising from corrosion, mechanical damage, fabrication flaws or weld boundaries. The circularity measurement and inspection requirements are currently addressed by partial tile removal. The cost of anechoic tile removal and replacement, as well as time spent in dry dock for submarines undergoing maintenance checks, provides an incentive to apply a through-tile inspection technique. However, the sound absorbing nature of the tiles hinders ultrasonic methods, combined with the tile-thickness challenge, severely limits the number of available non-destructive evaluation methods that can potentially provide accurate through-tile thickness or lift-off distance measurements.

Precise outer hull surface measurements can be achieved with a number of available spatial measurement technologies, including the Laser Tracked Ultrasonic Technology (LTUT), laser tracker, laser radar, or photogrammetry. In order to achieve an exact topology of the steel submarine hull beneath the tiles, an accurate measurement of the perpendicular distance from the submarine hull surface to the outer tile surface, i.e., lift-off distance is required. Such a dimension is necessary to affect a strategy of mathematical correction to a conventionally measured tile-surface or super-surface coordinates in order to characterize the true metal pressure-hull substrate.

In general, signal response in eddy current testing is always sensitive to lift-off, which is defined as the vertical distance of a probe to a conducting surface. Conventional eddy current technology is commonly used for high-accuracy thickness measurement of paint, cladding of different metals, or corrosion product thickness, but the range of sensitivity is currently limited to several mm. Sensitivity to lift-off decays exponentially, but nominally scales with the size of the probe diameter. Therefore, a larger diameter may be used to compensate for this loss.

Inspection through thick (>>10 mm) coatings for the surface topology measurements at high resolution cannot be done with current state of the art devices. One system is available to measure simple linear lift-off distance (offset) over a flat metal surface through a thick low conducting coating. There are a few commercially available systems capable of gross identification of corrosion patches under thick coatings. Various technologies are available for inspections when the metal surface is exposed by removal of the coating.

There is therefore a need for an improved eddy current sensor for precision lift-off distance measurements.

SUMMARY

According to an embodiment, there is provided a pulsed eddy current sensor for measurement of a lift-off distance over a surface of a metallic substrate (a metallic surface), the pulsed eddy current sensor comprising: a primary excitation coil to which are applied voltage pulses for generating primary magnetic fields, wherein an interaction of the primary magnetic fields with the metallic substrate produces secondary magnetic fields; and secondary pick-up probes, each of the secondary pick-up probes located at a different vertical distance from the metallic surface, the secondary pick-up probes used for measuring the primary and secondary magnetic fields and for producing a differential signal that is representative of the lift-off distance.

According to another embodiment of the sensor, the secondary pick-up probes are provided within the primary excitation coil.

According to another embodiment of the sensor, the secondary pick-up probes are vertically aligned.

According to another embodiment of the sensor, the primary excitation coil comprises one or more coaxial excitation coils.

According to another embodiment of the sensor, the secondary pick-up probes comprise a pair of secondary pick-up coils.

According to another embodiment of the sensor, one of the secondary pick-up coils is wound in a first direction and the other one of the secondary pick-up coils is wound in a second direction, opposite to the first direction, thereby subtracting a signal induced in the one of the secondary pick-up coils from another signal induced in the other one of the secondary pick-up coils thereby producing the differential signal.

According to another embodiment of the sensor, both secondary pick-up coils are wound in the same direction, but connected with opposing leads thereby subtracting a signal induced in the one of the secondary pick-up coils from another signal induced in the other one of the secondary pick-up coils thereby producing the differential signal.

According to another embodiment of the sensor, the secondary pick-up probes are connected separately to a differential amplifier that subtracts a signal induced in the one of the secondary pick-up probes from another signal induced in the other one of the secondary pick-up probes thereby producing the differential signal.

According to another embodiment of the sensor, wherein the secondary pick-up probes are connected together at a fixed distance and the pulsed eddy current sensor further comprises an adjustment mechanism for vertically adjusting the position of the secondary pick-up probes within the primary excitation coil for substantially balancing the secondary pick-up probes.

According to another embodiment, the sensor further comprises an adjustment mechanism for adjusting a distance between the secondary pick-up probes for substantially balancing the secondary pick-up probes.

According to another embodiment, the sensor further comprises a ferrite core provided within each one of the secondary pick-up probes.

According to another embodiment, there is provided a pulsed eddy current sensing system for measurement of a lift-off distance over a surface of a metallic substrate (a metallic surface), the pulsed eddy current sensing system comprising: a pulse generator for generating voltage pulses; a primary excitation coil to which are applied voltage pulses for generating primary magnetic fields, wherein an interaction of the primary magnetic fields with the metallic substrate produces secondary magnetic fields; and secondary pick-up probes, each of the secondary pick-up probes located at a different vertical distance from the metallic surface, the secondary pick-up probes used for measuring the primary and secondary magnetic fields and for producing a differential signal that is representative of the lift-off distance.

According to another embodiment, the pulsed eddy current sensing system may further comprise an amplifier and a filter for removing high frequency noise components from the differential signal.

According to another embodiment, the pulsed eddy current sensing system may further comprise a local degaussing circuit for neutralizing a residual magnetization in the metallic surface.

According to another embodiment, the pulsed eddy current sensing system may comprise separate amplifiers for each secondary pick-up probe for substantially balancing the secondary pick-up probes.

According to another embodiment of the system, the secondary pick-up probes are provided within the primary excitation coil.

According to another embodiment of the system, the secondary pick-up probes are vertically aligned.

According to another embodiment, there is provided a method for mapping a metallic surface under a low conductivity coating, a distance from the top of the low conductivity coating to the metallic surface defining a lift-off distance. The method comprises: performing a series of measurements of the lift-off distance (depth) at reference positions covering two dimensions (latitude and longitude) over the low conductivity coating; and integrating the series of measurements with the reference positions to produce a three-dimensional map of the metallic surface under a low conductivity coating.

According to another embodiment of the method, the performing of one of the series of measurements at one of the reference positions comprises: generating a primary magnetic field centered on a vertical axis normal to the metallic surface at the one of the reference positions, wherein an interaction of the primary magnetic field with the metallic surface produces a secondary magnetic field; measuring the primary and secondary magnetic fields at two distinct vertical positions on the vertical axis; and from the measured primary and secondary magnetic fields, calculating a differential signal that is representative of the lift-off distance.

The term "dielectric" is intended to mean an electrical insulator that can be polarized by an applied electric field. When a dielectric is placed in an electric field, electric charges do not flow through the material as they do in a conductor, but only slightly shift from their average equilibrium positions causing dielectric polarization. Because of dielectric polarization, positive charges are displaced toward the field and negative charges shift in the opposite direction. This creates an internal electric field which reduces the overall field within the dielectric itself.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

In embodiments discussed herein, there are disclosed a pulsed eddy current sensor for precision lift-off distance measurement and a method for precision lift-off distance measurement.

In comparison with a conventional eddy current inspection technology, in which the magnetic field is generated by a sinusoidal voltage applied to a coil, a pulsed eddy current (PEC) sensor, or a transient eddy current sensor, uses voltage pulses to excite a coil.

Figure 1:
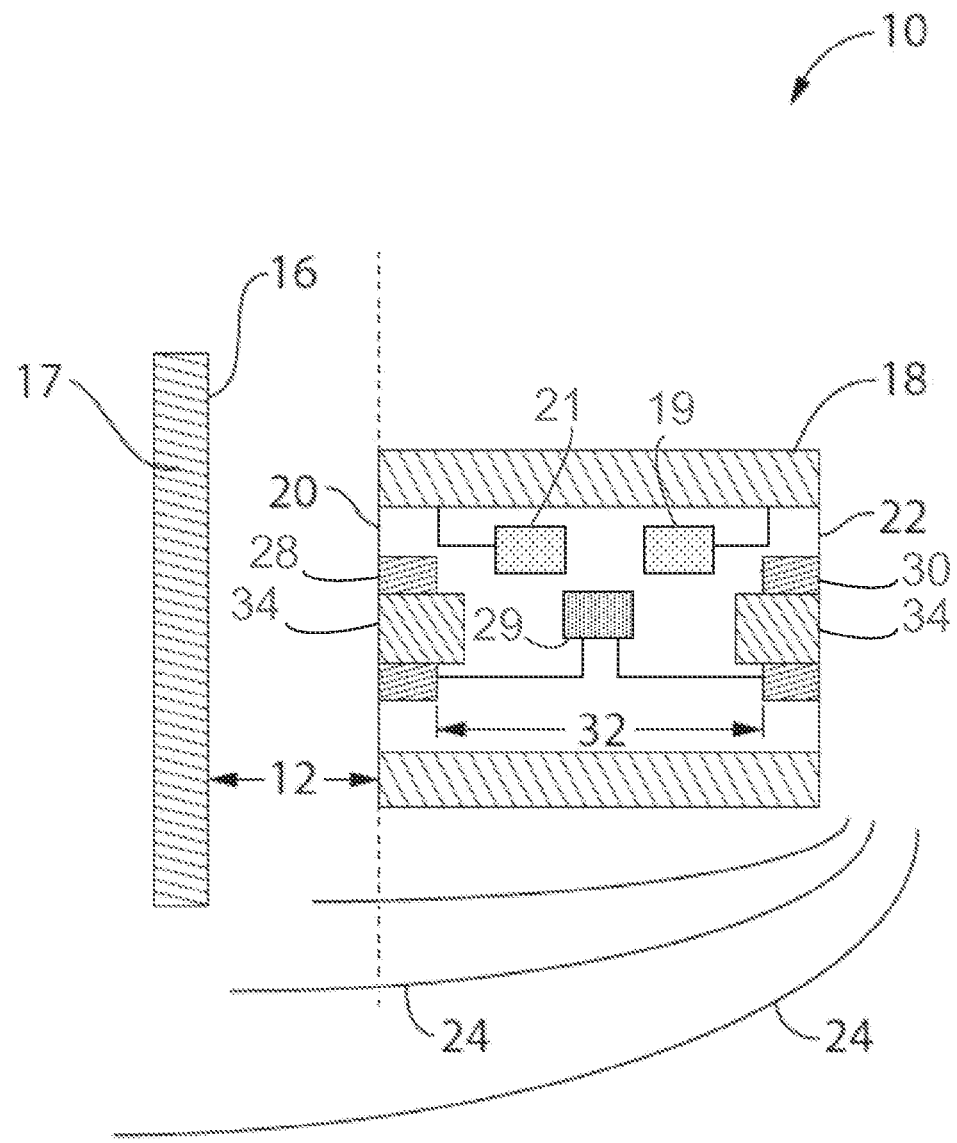
FIG. 1 is a schematic cut-out illustration of a pulsed eddy current sensor in accordance with an embodiment.
Figure 2:
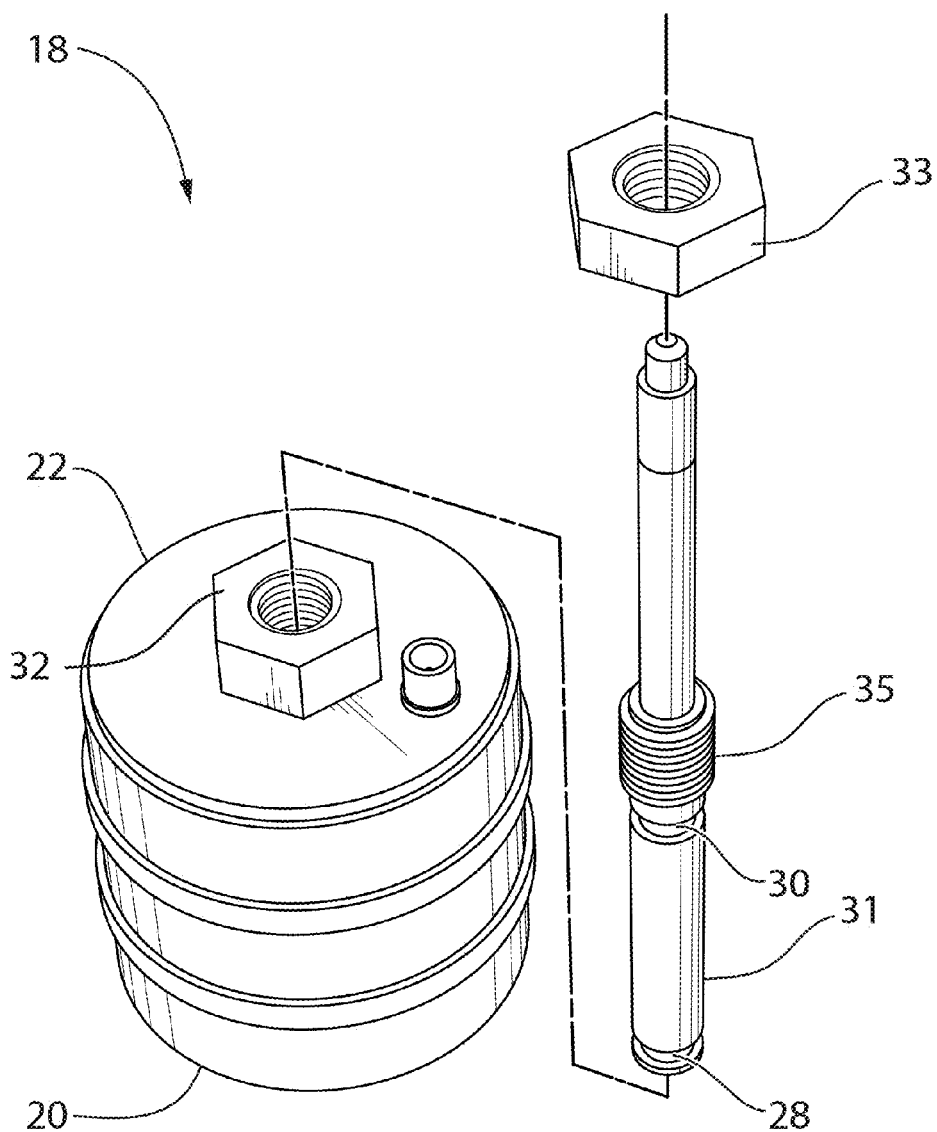
FIG. 2 is a perspective view showing a disassembled pulsed eddy current sensor in accordance with another embodiment.
Figure 3:
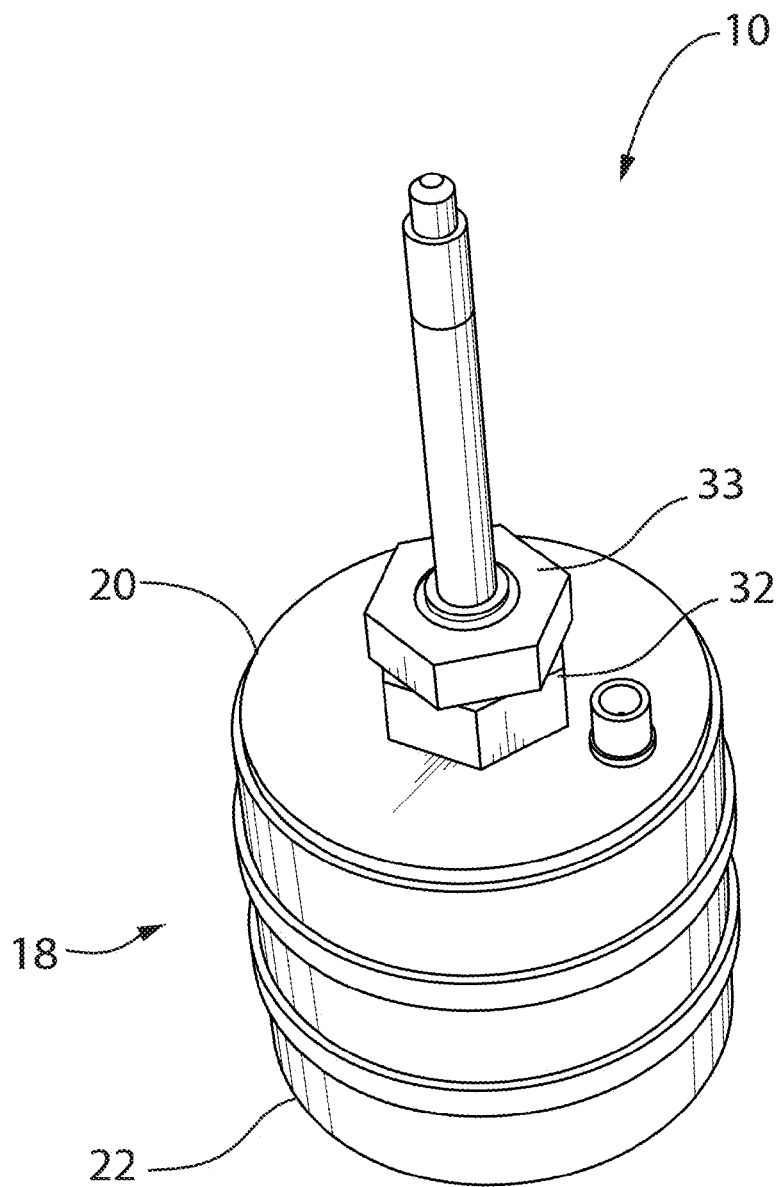
FIG. 3 is a perspective view showing the pulsed eddy current sensor of FIG. 2 assembled.

Referring now to the drawings and more particularly to FIGS. 1, 2 and 3, there is shown a pulsed eddy current sensor 10 positioned at a distance, called lift-off distance 12, from the metallic surface 16. The pulsed eddy current sensor 10 is for measurement of a lift-off distance 12 of a non- or low-conducting coating 14 (e.g., an insulator material or a dielectric material) over a metallic surface 16 of a metallic substrate 17. The pulsed eddy current sensor 10 is also used for detection of defects on the metallic surface 16 through the low conducting coating 14 as well as the 2D and/or 3D mapping of the metallic surface 16.

The pulsed eddy current sensor 10 includes a primary excitation coil 18 having opposite ends 20, 22. One of the opposite ends 20 is for interfacing with the low conducting coating 14. The primary excitation coil 18, to which are applied voltage pulses, is for generating a primary magnetic field 24, which in turn creates a plurality of pulsed eddy currents in the metal and magnetization of the metal (if it is ferromagnetic). These eddy currents and magnetization, if present, in turn produce a secondary magnetic field (i.e., an interaction of the primary magnetic field with the metallic substrate 17 produces the secondary magnetic field) between metallic surface 16 and the pulsed eddy current sensor 10. The pulsed eddy current sensor 10 also includes secondary pick-up probes 28, 30 located within the primary excitation coil 18. The secondary pick-up probes 28, 30 are used for measuring the primary and secondary magnetic fields and for producing a differential signal that is representative of the lift-off distance.

According to an embodiment, the secondary pick-up probes 28, 30 are provided within the primary excitation coil 18. In an embodiment, the secondary pick-up probes 28, 30 are horizontally aligned with the bottom end of the primary excitation coil 18. Furthermore, the secondary pick-up probes 28, 30 are vertically, however, it is not a need for the secondary pick-up probes 28, 30 to be within the primary excitation coil 18. In an embodiment, the secondary pick-up probes 28, 30 are centered within the primary excitation coil 18.

According to an embodiment, the secondary pick-up probes 28, 30 include a pair of secondary pick-up coils.

According to another embodiment the secondary pick-up probes 28, 30 include Giant magnetoresistance (GMR) magnetic sensors Anisotropic magnetoresistance (AMR) sensors and Hall sensors, or a combination thereof.

Secondary pick-up coil may be wound in a first direction (not shown) and the other one secondary pick-up coil 30 may be wound in a second direction (not shown), opposite to the first direction. This allows the subtraction of a signal induced in the secondary pick-up coil from another signal induced in the other secondary pick-up coil thereby producing the differential signal. Thus, the plurality of pulsed eddy currents and magnetization in the case of a ferromagnetic substrate produce a secondary magnetic field and the secondary magnetic field is detected by the secondary pick-up coils for providing measurement of the lift-off distance 12 of the low conducting coating 14 over the metallic surface 16.

According to another embodiment, the pulsed eddy current sensor 10 may be configured such that both secondary pick-up coils are wound in the same direction, but connected with opposing leads. This configuration may allow subtracting a signal induced in the one of the secondary pick-up coils from another signal induced in the other one of the secondary pick-up coils thereby producing the differential signal.

According to another embodiment, the pulsed eddy current sensor 10 may be configured such that the secondary pick-up probes 28, 30 are connected separately to a differential amplifier 29 that subtracts a signal induced in the one of the secondary pick-up probes 28 or 30 from another signal induced in the other one of the secondary pick-up probes 28 or 30 thereby producing the differential signal.

According to an embodiment, the secondary pick-up probes 28, 30 may be connected together at a fixed distance and the vertical position may be adjusted within the primary excitation coil 18 for substantially balancing the secondary pick-up probes. The secondary pick-up probes 28, 30 may be adjustable relative to the metallic surface 16 using an adjustment mechanism such as a screw mechanism (e.g., threads 35 at the top of spindle 31, adjustment nut 32 and locking nut 33). Indeed, the secondary pick-up probes 28, 30 may be fixed on a spindle 31 and fixed relative to each other. It may be advantageous to minimize the differential signal in air to maximize sensitivity to the substrate.

According to an embodiment and still referring to FIG. 1, a distance 32 between the secondary pick-up probes 28, 30 may be adjustable for minimizing a differential signal in air, and thereby substantially balancing the secondary pick-up probes 28, 30. In this embodiment, the adjustment mechanism could be a screw type arrangement on the spindle for either one or both pick-up probes or a sliding and locking mechanism for adjusting the vertical height of either one or both pick-up probes.

According to another embodiment and still referring to FIGS. 1, 2 and 3, the pulsed eddy current sensor comprises a ferrite core 34 provided within each of the secondary pick-up probes 28, 30 respectively.

According to an embodiment, adjustment may be performed away from any conducting or magnetic objects that may be sensed by the secondary pick-up probes 28, 30. At the time of measurement, when one end 20 of the pulsed eddy current sensor 10 is positioned near a conducting or magnetic material, an imbalance between the secondary pick-up probes 28, 30 develops resulting in an increase of the differential signal.

Figure 4A:
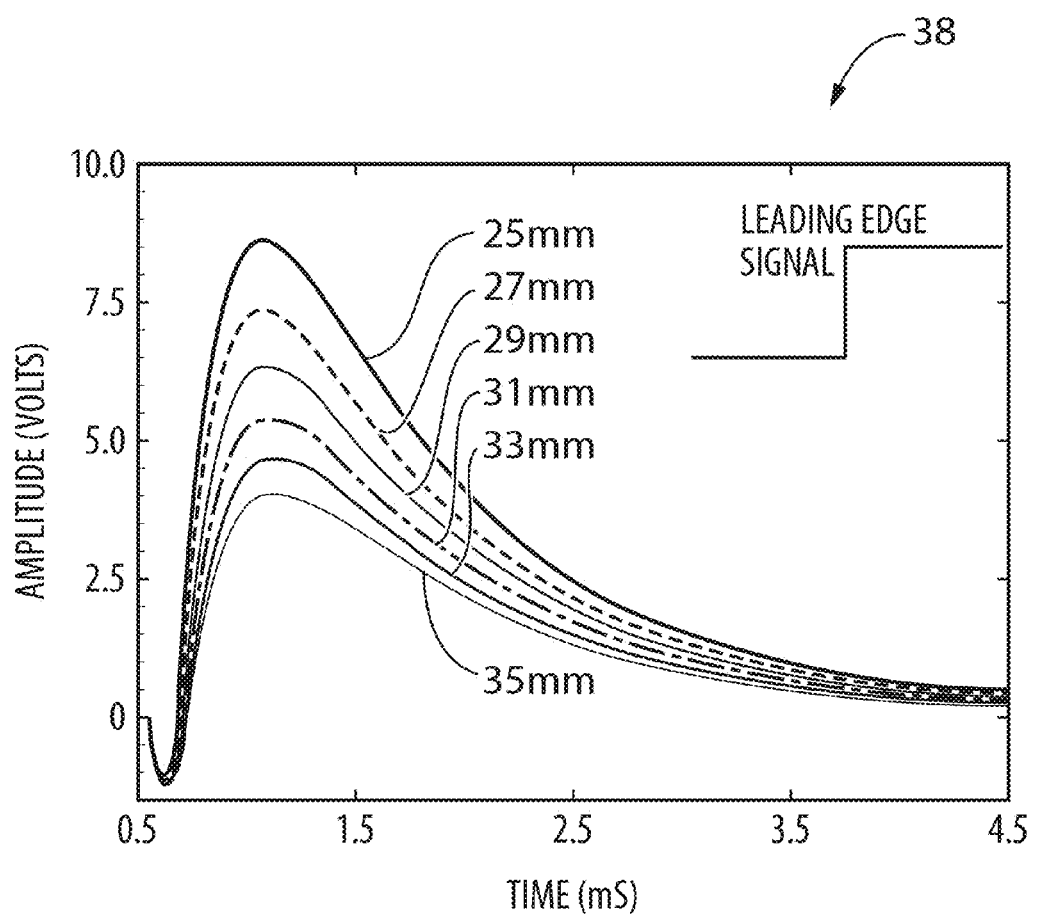
FIG. 4A is a graph which illustrates a differential probe response to the leading edge of a rectangular pulse from 25 mm to 35 mm lift-off distance from a metallic substrate at 2 mm intervals in a laboratory setting in accordance with an embodiment.

According to another embodiment, voltage pulses comprise a plurality of rectangular pulses 38 having a leading edge such as shown in FIG. 4A, without limitation. Each one of the plurality of rectangular pulses 38 may include a pulse width (not shown) and wherein the pulse width is longer than a transient response of the system which includes the pulsed eddy current sensor 10 and metallic surface 16. Therefore, the rectangular pulse 38 generates two separated-in-time pulses of eddy current within the sample (i.e. metallic substrate 17). The pulsed eddy currents and magnetization for the case of a ferromagnetic substrate generate a secondary magnetic field which combined with the primary field 18 is detected by one or more of at least two secondary pick-up probes 28, 30.

According to an embodiment, the primary excitation coil 18 may include one or more coaxial excitation coils.

Referring now to FIGS. 2 and 3, there are shown a disassembled pulsed eddy current sensor 10 and an assembled pulsed eddy current sensor 10 respectively. FIG. 2 shows the primary excitation coil 18, and the secondary pick-up probes 28, 30 for insertion within the primary excitation coil 18. Primary excitation coils 18 having an internal diameter between 1"⅞ to 2"½ have been shown to work. FIG. 3 pulsed eddy current sensor 10 when the secondary pick-up probes 28, 30 (not visible) are installed within the primary excitation coil 18.

Figure 4B:
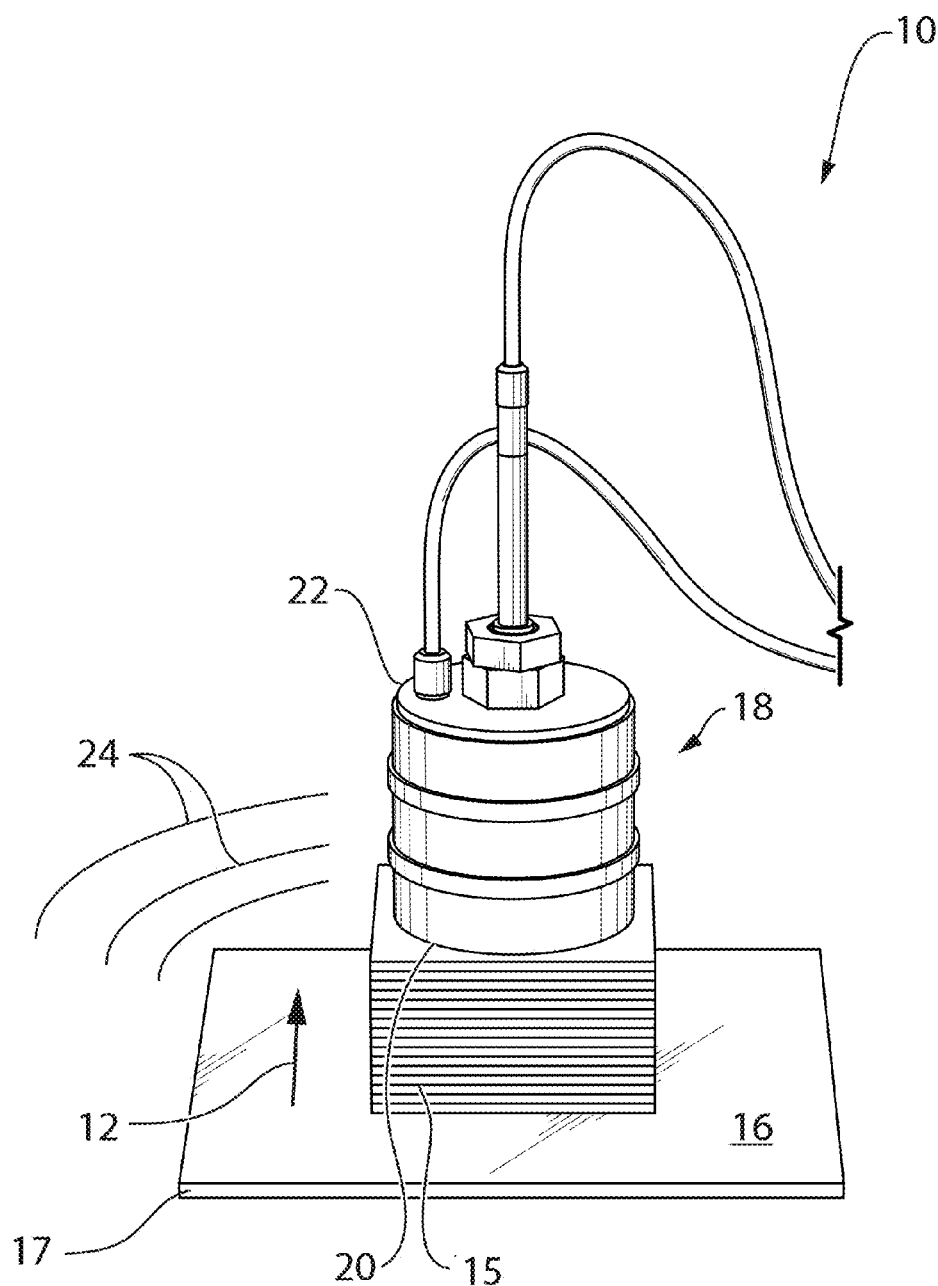
FIG. 4B is a picture illustrating a test where a pulsed eddy current sensor is positioned on a plurality of low conducting coatings and provides the lift-off distance increments over a metallic substrate.

FIG. 4A is a graph which illustrates a differential probe response to the leading edge of a rectangular pulse from 25 mm to 35 mm lift-off distance from a metallic substrate 17 at 2 mm intervals in a laboratory setting. FIG. 4B illustrates a pulsed eddy current sensor 10 positioned on a plurality of low conducting tiles 15, i.e., on the low conducting coating which provides the lift-off distance 12 increments over the metallic surface 16.

According to another embodiment, there is provided a pulsed eddy current sensing system for measurement of a lift-off distance 12 over a surface 16 of a metallic substrate 17. The pulsed eddy current system may include a pulse generator 19 for generating voltage pulses. The pulsed eddy current system may also include a primary excitation coil 18 to which are applied voltage pulses for generating primary magnetic fields 24, which induce pulsed eddy currents in the metallic substrate 17, the pulsed eddy currents producing secondary magnetic fields. The pulsed eddy current system also includes secondary pick-up probes 28, 30, where each of the secondary pick-up probes 28, 30 are located at a different vertical distance from the metallic surface 16 and where the secondary pick-up probes 28, 30 are used for measuring the primary and secondary magnetic fields and for producing a differential signal that is representative of the lift-off distance 12.

An amplifier and a filter (not shown) located downstream from the secondary pick-up probes 28, 30 are used.

According to an embodiment, the pulsed eddy current system may further include an amplifier (not shown) and a filter (not shown) to amplify and filter the differential signal from the secondary pick-up probes 28, 30 thereby removing high-frequency noise components from the differential signal. The pulsed eddy current system may further include a local degaussing circuit 21 for neutralizing a residual magnetization in the metallic surface 16.

According to another embodiment, the pulsed eddy current system described above may include separate amplifiers (not shown) for each secondary pick-up probe 28 or 30 for substantially balancing the secondary pick-up probes 28, 30.

It is to be noted that the pulsed eddy current sensor 10 can serve as an adjunct to existing metrology systems such as, without limitations, photogrammetry, laser tracker, articulating metrology arm, and the like, to allow 3D mapping/reverse engineering of substrate surfaces, i.e. metallic surface, that are otherwise inaccessible due to presence of a low conducting coating.

The design of the pulsed eddy current probe is optimized to obtain a required precision, sensitivity, and signal-to-noise ratio most notably by use of adjustable upper secondary pick-up probe and local degaussing ability for operation over ferromagnetic substrates, such as submarine hulls, or pressure vessels and piping used in oil and gas processing or power generation systems.

The use of the pulsed eddy current sensor 10 to perform lift-off distance measurements demonstrates lift-off distance 12 measurement accuracy to better than ±0.5 mm at a nominal lift-off distance 12 of 30 mm of low conducting coating 14. FIG. 4A shows the signal response for lift-off distances 12 in this range (25, 27, 29, 31, 33 mm). It also demonstrates the capability to detect a 3 mm deep and 20 mm diameter feature at this specific lift-off distance 12.

According to an embodiment, there is provided a method for mapping a metallic surface 16 under a low conductivity coating 14. The method includes the step of taking a series of measurements of the lift-off distance over a surface of a metallic substrate (a metallic surface) using a pulsed eddy current sensor 10. Between measurements, the pulsed eddy current sensor 10 is displaced over the low conducting coating 14 according to a reference pattern. The reference pattern includes the 3D coordinates of the position of the pulsed eddy current sensor 10 over the low conducting coating 14. The position of the pulsed eddy current sensor 10 is normally the center of the bottom of the secondary pick-up probe 28.

The reference pattern can be comprised of substantially straight lines such that a profile of the metallic surface 16 in a plane can be established. The reference pattern can also be determined by existing commercial measurement systems which can give the precise location of a measurement point of the pulsed eddy current sensor 10 (its "position") at all times.

The lift-off measurements are performed using the pulsed eddy current sensor 10 in the manner described earlier.

Figure 9A:
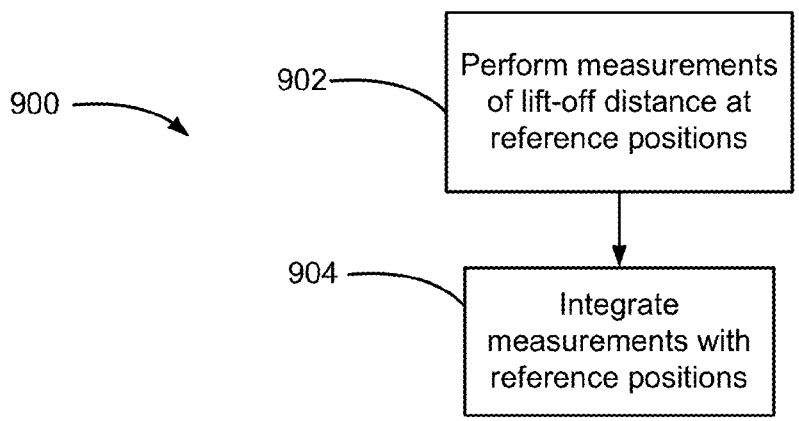
FIG. 9A is a flowchart showing a method for three-dimensional mapping of a metallic surface under a low conductivity coating according to an embodiment.

Now referring to FIG. 9A, a method 900 for mapping a metallic surface under a low conductivity coating, wherein a distance from the top of the low conductivity coating to the metallic surface defines a lift-off distance. The method 900 comprises: performing a series of measurements of the lift-off distance (depth) at reference positions covering two dimensions (latitude and longitude) over the low conductivity coating (step 902); and integrating the series of measurements with the reference positions to produce a three-dimensional map of the metallic surface under a low conductivity coating (step 904).

Figure 9B:
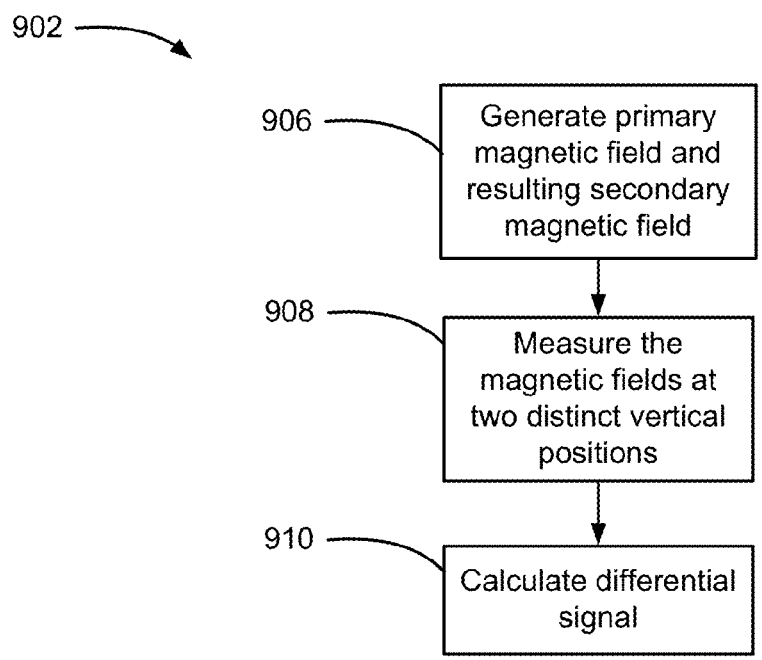
FIG. 9B is a flowchart showing the step of performing of one of the series of measurements at one of the reference positions from the method of FIG. 9A.

Now referring to FIG. 9B, the step 902 of performing of one of the series of measurements at one of the reference positions is detailed. Step 902 comprises generating a primary magnetic field centered on a vertical axis normal to the metallic surface at the one of the reference positions, wherein an interaction of the primary magnetic field with the metallic surface produces a secondary magnetic field (step 906); measuring the primary and secondary magnetic fields at two distinct vertical positions on the vertical axis (step 908); and from the measured primary and secondary magnetic fields, calculating a differential signal that is representative of the lift-off distance (step 910).

Figure 5:
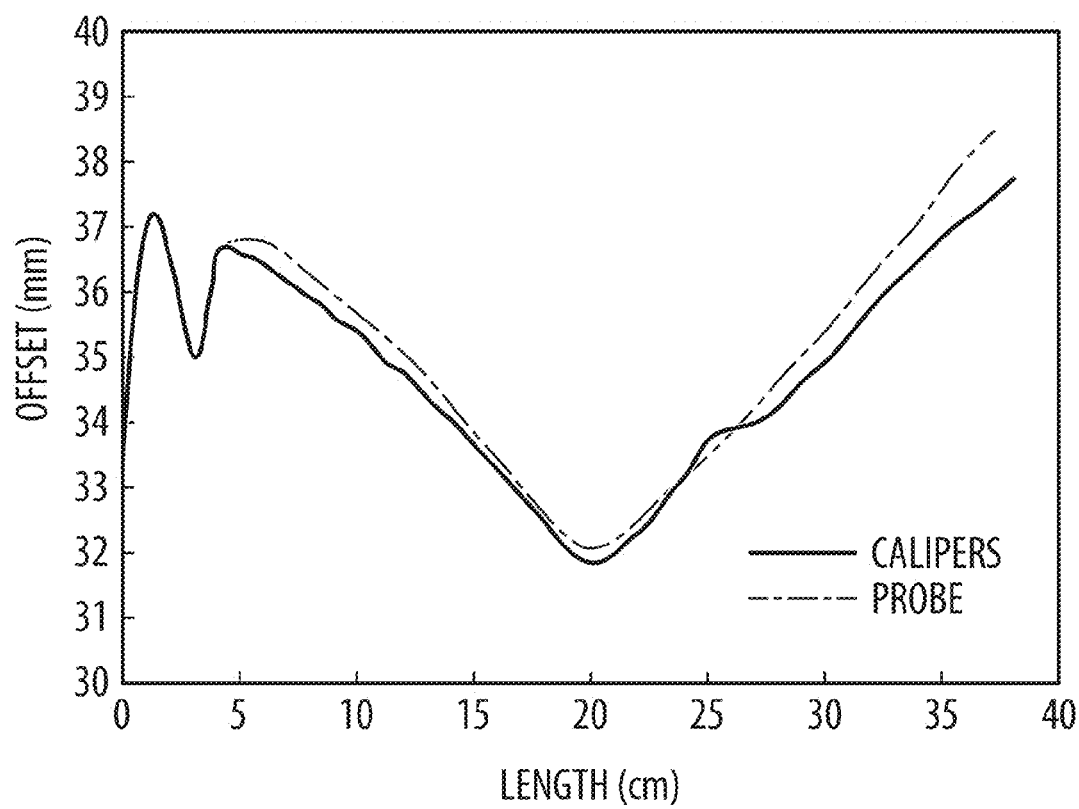
FIG. 5 is a graph showing lift-off distance measurements (offset) as measured from a flat datum over a dented metal plate using a 3" excitation coil for comparison with vernier caliper reference datum.

Now turning to FIG. 5, there is shown the relationship between lift-off distance measurements (offset) and the distance on a straight line as measured from a flat datum over a dented metal plate using a 3" excitation coil for comparison with vernier caliper reference datum. This is an example of 2D mapping of a metallic surface. In order to obtain a 3D map of the metallic surface according to an embodiment, a plurality of measurements such as the ones shown in FIG. 5, taken along a plurality of parallel straight lines, each providing probe location, are integrated into a 3D modeling software. The 3D modeling software will produce the 3D model of the metallic surface. In this particular case, location and orientation of probe is required.

The pulsed eddy current sensor may be used in different applications, such as, without limitations, submarine hull inspections (circularity measurements, under tile corrosion detection, geometric characterization) and presents clear cost savings. Other possible applications include, without limitations, metallic substrate inspection of polymer-armoured vehicles, composite reinforced structure, thermal protected structure, radar absorbent coated airframes and the like.

Figure 6A:
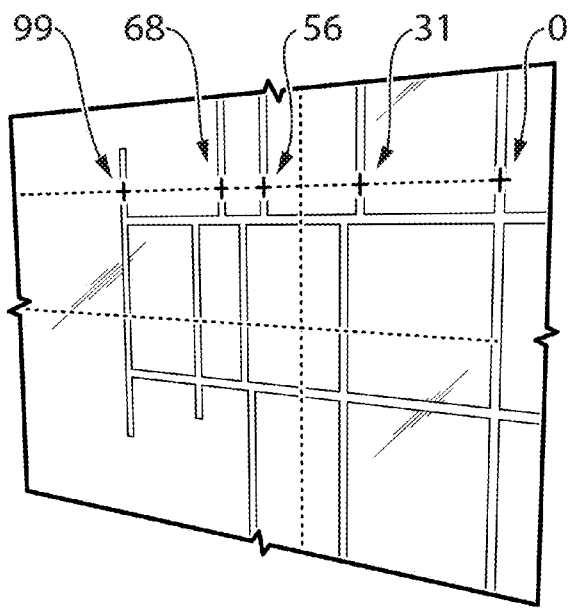
FIG. 6A is a picture illustrating an upper dotted line with numbered demarcations (cm) which shows the low conducting coating path measured by the pulsed eddy current sensor with underlying metallic substrate profile shown as black line in FIG. 6B in accordance with another embodiment (white lines mark the low conducting tile boundaries)
Figure 6B:
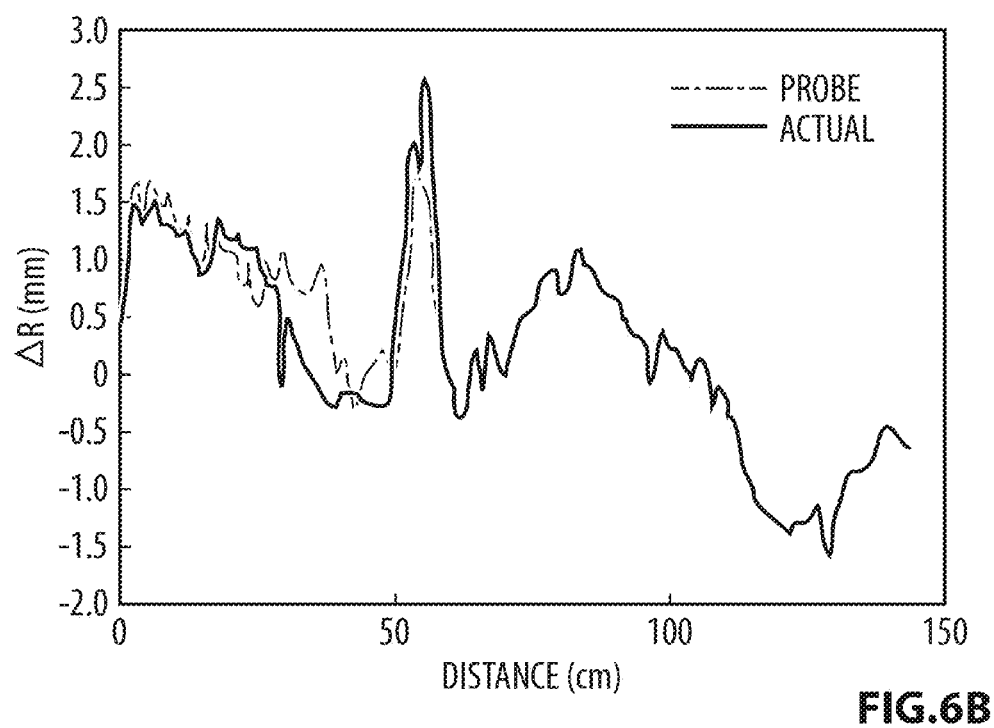
FIG. 6B is a graph which illustrates a metallic surface profile along FIG. 6A line interpreted from a pulsed eddy current sensor, compared with a Laser Tracked Ultrasonic direct measurement of surface profile low conducting coating was off.

FIG. 6A illustrates an upper dotted line with numbered demarcations (in cm) which shows the low conducting coating path measured by the pulsed eddy current sensor 10 with underlying metallic substrate profile shown as a continuous black line in FIG. 6B. "White" lines on FIG. 6A mark the low conducting tile boundaries. FIG. 6B is a graph which illustrates a metallic surface profile along FIG. 6A line interpreted from a pulsed eddy current sensor, compared with a Laser Tracked Ultrasonic direct measurement of surface profile low conducting tiles were off. FIG. 6A and FIG. 6B will be more readily understood by referring to the following examples 1 and 2.

To avoid the cost of penetration or removal and subsequent repair of the coating to access the objective metal inspection surface, there is a need for a sensor that can measure the vector from the commercial systems closest possible measurement point on or over the coating, to that point of interest on the underlying metallic substrate. Using this so called stand-off or lift-off distance, a mathematical correction can be applied to the coordinate provided by the commercial system to establish the true coordinate on the hidden substrate. Such a device effectively extends the "reach" of the commercial system to access the hidden surface through the coating, while avoiding the costs of physical penetration and repair.

The present invention will be more readily understood by referring to the following examples which are given to illustrate the invention rather than to limit its scope.

EXAMPLE 1

Laboratory Tests

According to a first example and returning to FIG. 4A, there is shown the differential probe response to the leading edge of the rectangular pulse at various lift-off distances from a metallic substrate, which is used to simulate a submarine hull. The pulsed eddy current is calibrated by stacking, i.e., 1 mm thick, plastic sheets under the pulsed eddy current and taking measurements (voltage response to lift-off distance) as each additional plastic sheet is inserted. More particularly, FIG. 4A shows differential probe response to the leading edge of the rectangular pulse from 25 mm to 35 mm lift-off distance from the metallic surface at 2 mm intervals. Instead of the signal from the leading edge, the signal from the trailing edge of the pulse, which is essentially an inverted form of that from the leading edge, can also be used. Alternatively, the signal from both the leading edge and the trailing edge can be combined and the peak-to-peak signal can be used.

Figure 7A:
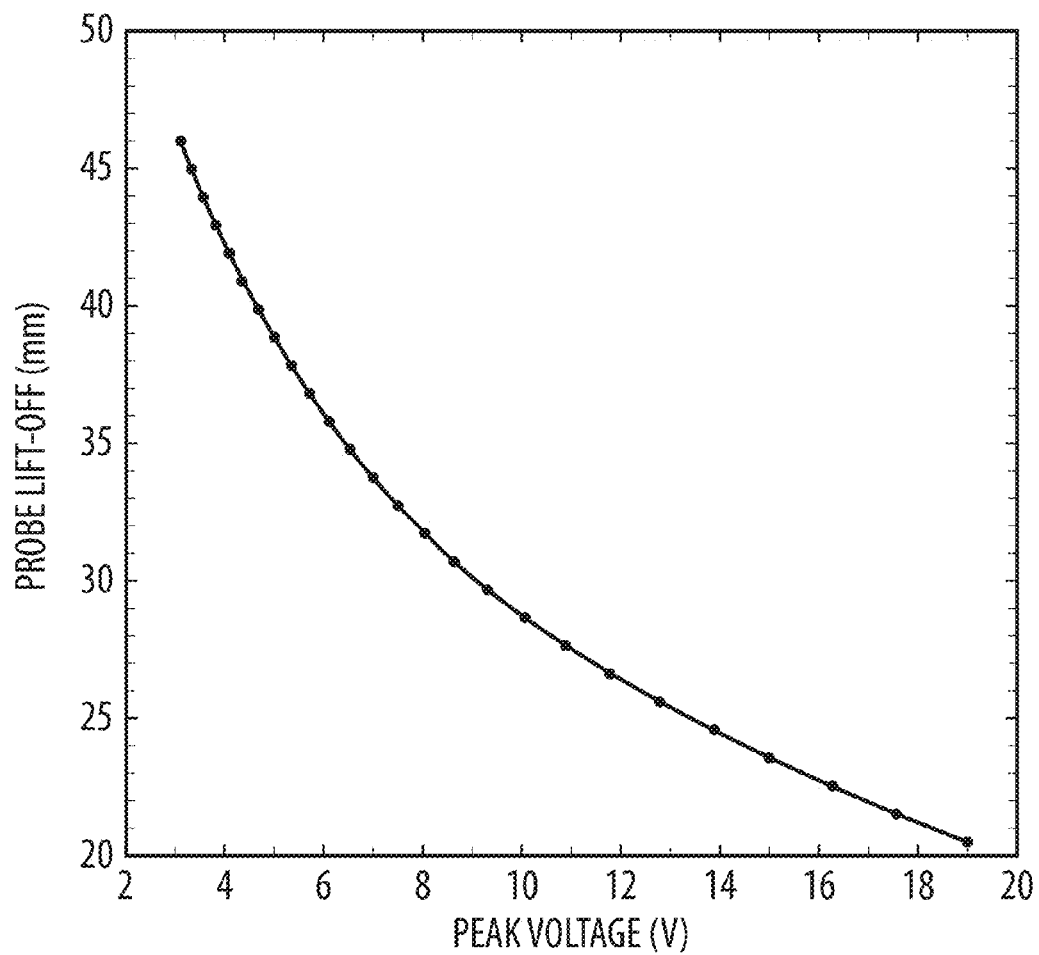
FIG. 7A is a graph which illustrates a calibration curve for conversion of voltage response to lift-off distance of FIG. 4A, where the solid curve shows a cubic polynomial fit to the data.

FIG. 7A shows a calibration curve for conversion of voltage response to lift-off distance based on the peak-to-peak response. Solid curve represents a cubic polynomial fit to the data (other functions could be used). More particularly, FIG. 7A shows how the peak-to-peak signal response varies with gradually increasing lift-off distance up to 45 mm, covering the range of values found on the hull. It is to be noted that FIGS. 4A and 7A are not the same calibration and FIG. 7a is a peak-to-peak measurement of lead and trailing edge. Leading edges, trailing edges or combination of the two edges could be used.

Laboratory tests of the system exploited by the pulsed eddy current sensor demonstrate that the signal noise level corresponded to only 0.03 mm at a lift-off distance of 35 mm. This noise level is essentially independent of lift-off distance. However, the signal increased approximately exponentially with inverse lift-off distance, so the signal-to-noise ratio is substantially better at smaller lift-off distances. The pulsed eddy current sensor's sensitivity is sufficient to detect a 1.5 cm diameter and 3 mm deep flat-bottom hole in a steel plate as shown in FIG. 7B.

Figure 7B:
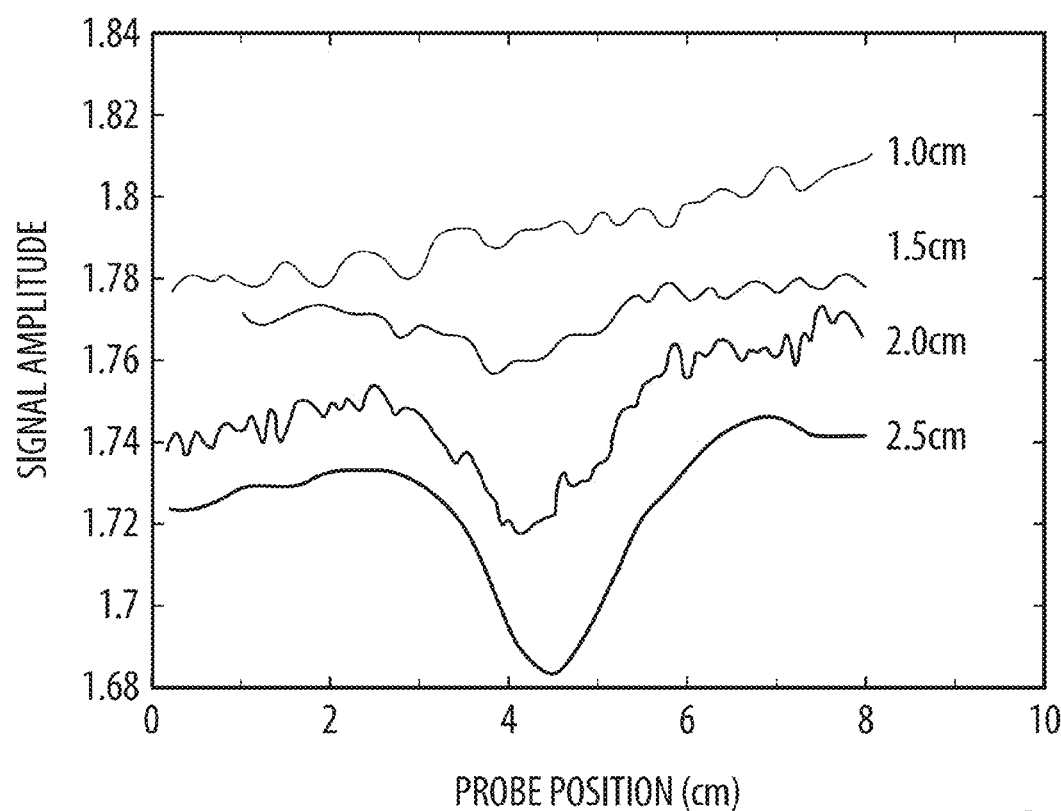
FIG. 7B is a graph which illustrates line-scans over flat bottom holes of different diameters where the holes are 3 mm deep and the scans are shifted vertically for clarity in accordance with another embodiment.
Figure 7C:
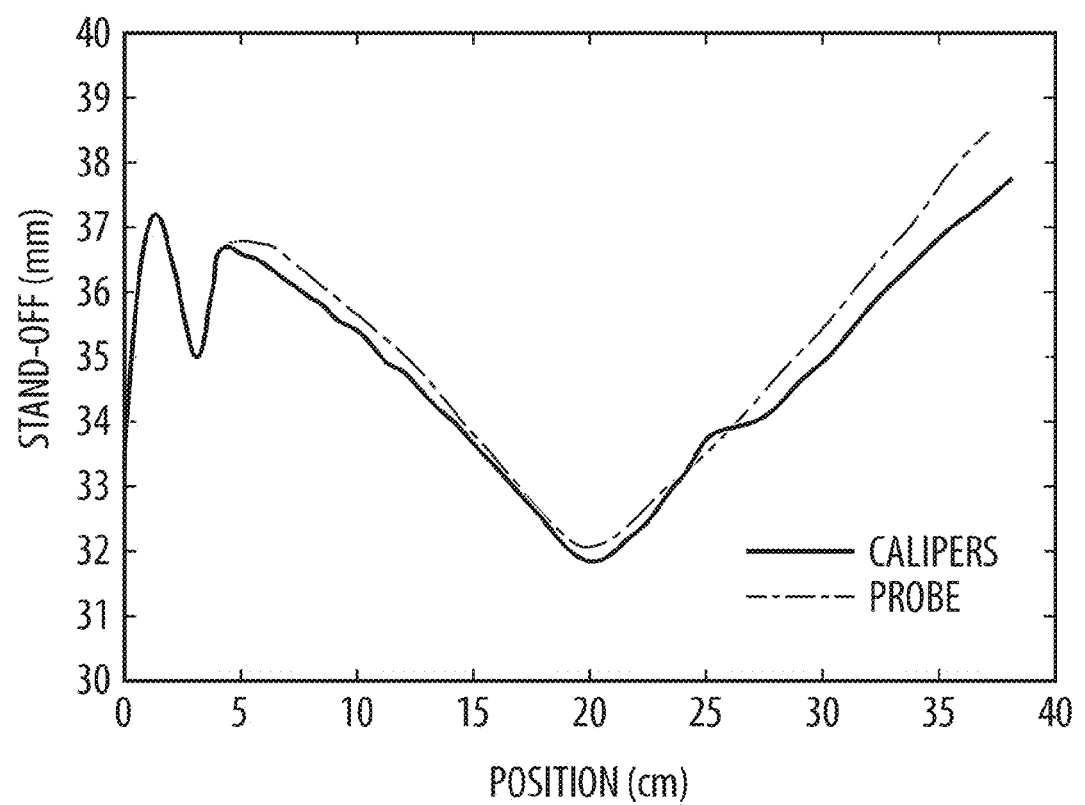
FIG. 7C is a graph which illustrates lift-off distances from deformed plate obtained with a pulsed eddy current sensor and measured directly with a caliper in accordance with another embodiment.

Referring now to FIG. 7B, there are shown line-scans over flat-bottom holes of different diameters. The holes are 3 mm deep. The scans are shifted vertically for clarity. It is to be noted that the pulsed eddy current also performs well in mapping surface topology of a deformed steel plate. FIG. 7C compares pulsed eddy current lift-off distance measurements with lift-off distance measurements made with a conventional caliper. As can be seen, the correct sample profile, to within 1 mm, is obtained.

EXAMPLE 2

Field Tests

Figure 8A:
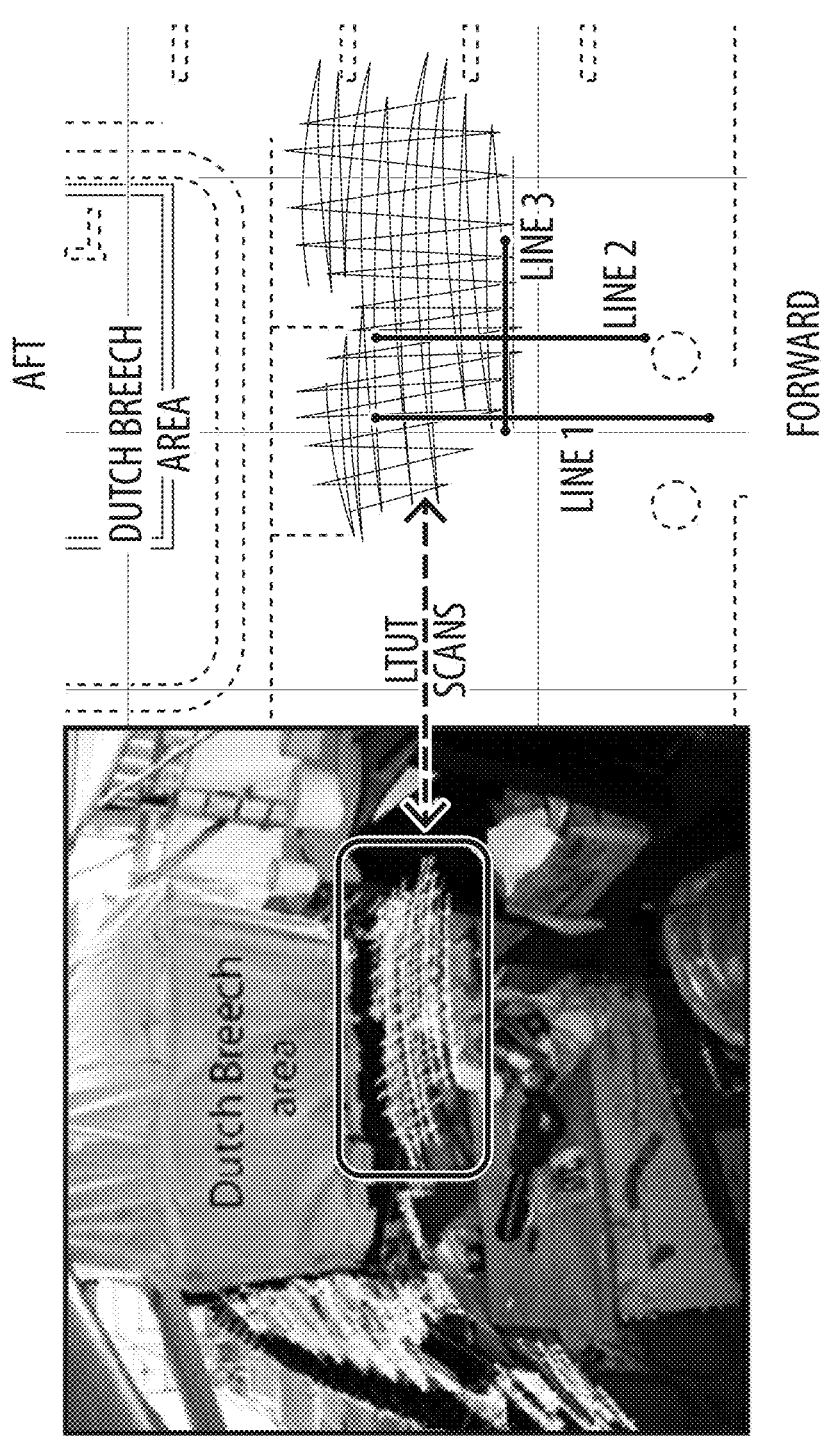
FIG. 8A picture with a corresponding schematic drawing that illustrate hull regions of the steel surface used in a field test in accordance with another embodiment.

According to another example, the pulsed eddy current sensor is tested on a dry docked submarine in an area with a previously characterized hull surface, which is now covered with anechoic tiles, a particular low conducting tile. FIG. 8A shows the test location, the profiled area and lines along which the pulsed eddy current sensor and complementary laser profiler measurements were performed. The first measurements on the hull of the submarine are conducted along a line parallel to the axis of the sub, near top dead centre (lines 1 and 2 in FIG. 8A). Then measurements are performed in the hull circumferential direction (line 3 in FIG. 8A).

Figure 8B:
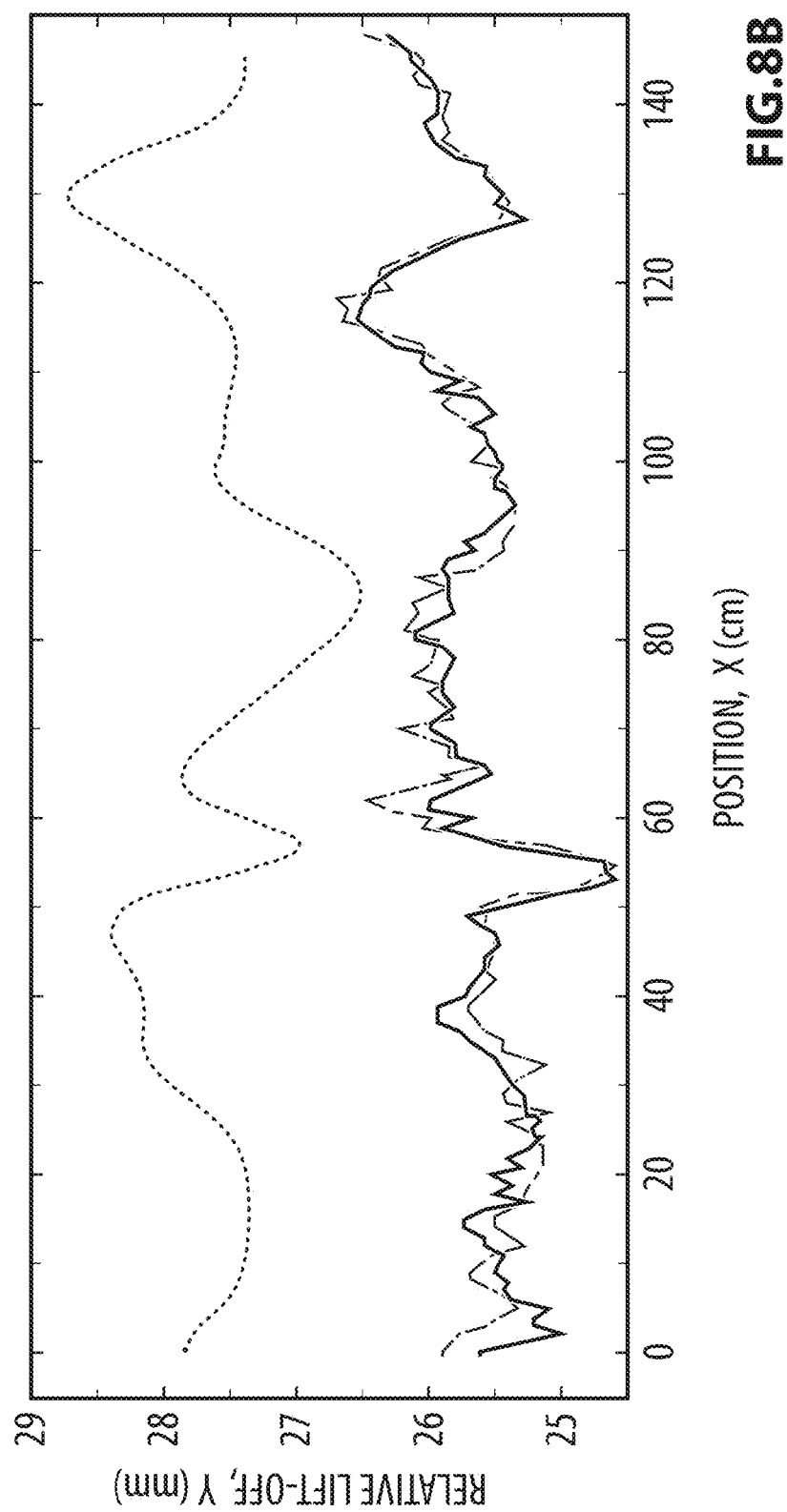
FIG. 8B is a graph illustrating relative lift-off distance data collected in the first region, where the dotted and solid curves are presents pulsed eddy current sensor lift-off distances from the steel surface of FIG. 8A under tiles, and where the dashed curve illustrates the smoothed lift-off distance profile of the laser-profiler.

A laser profiler is used to measure lift-off distances to the tile surface from a straight bar. FIG. 8B demonstrates the testing procedure on the example of line 1. The hull is scanned twice along this line at 1 cm intervals to obtain the distance from the top of the tiles to the hull. During the first scan, i.e., the dotted curve, local demagnetization functionality of the pulsed eddy current sensor is disabled intentionally. In order to determine the steel surface profile, the pulsed eddy current sensor lift-off distance data, i.e., the local thickness of the tiling is subtracted from the profile of the tile surface, i.e., the smoothed and inverted lift-off distance data from the laser profiler, the dashed curve in FIG. 8B. More particularly, FIG. 8B shows relative lift-off distance data collected in the first region, where the dotted and solid curves presents pulsed eddy current sensor lift-off distances from the steel surface under the tiles. On the other hand, the dashed curve is the smoothed lift-off distance profile of the laser-profiler, defined up to a vertical shift constant.

Figure 8C:
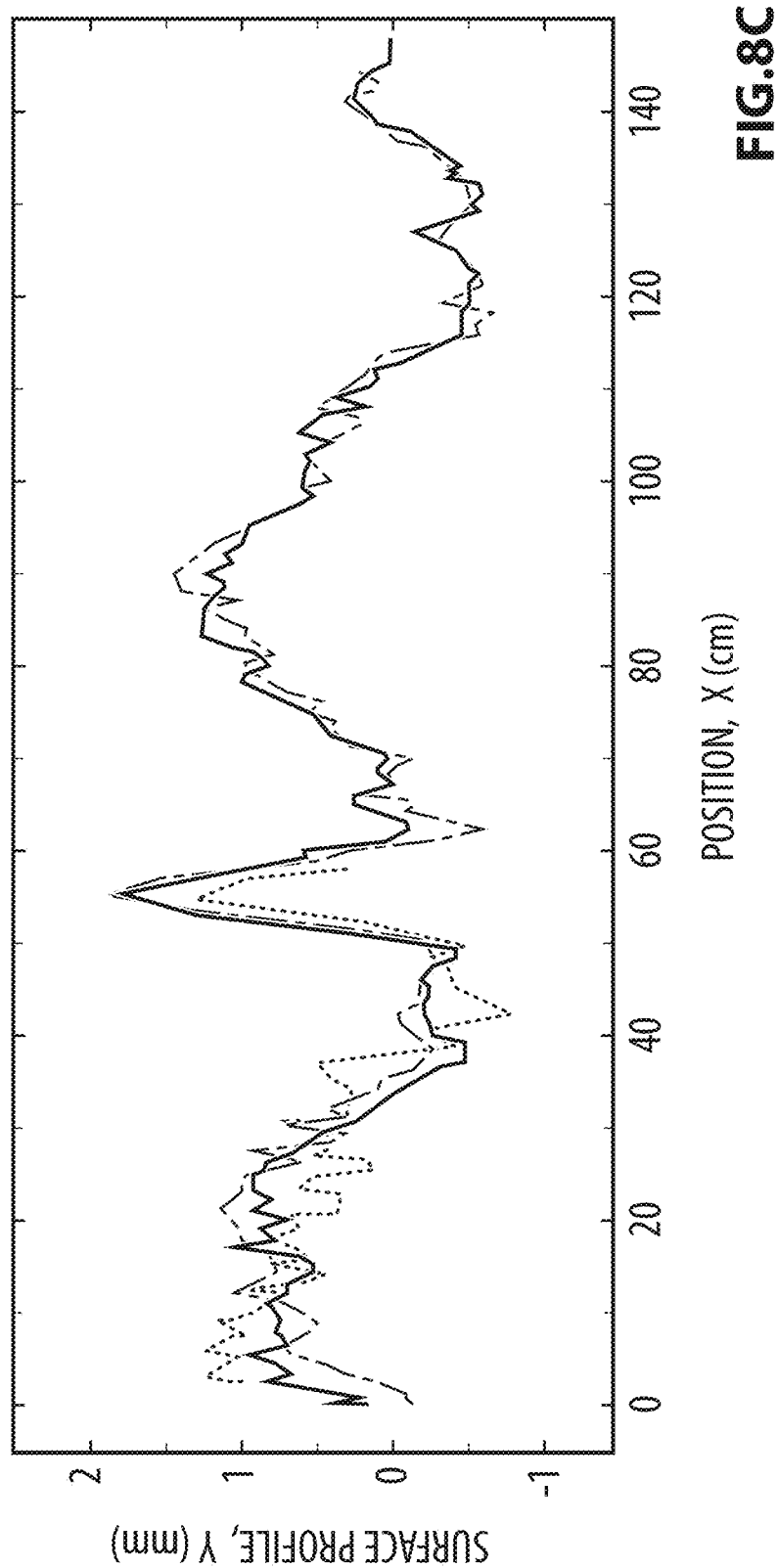
FIG. 8C is a graph of the profile of the steel surface under the first scanned region where the light-dotted and solid lines presents profiles obtained with and without local demagnetization, respectively and where the dashed line shows the actual profile of the steel surface where the topology data are available from 0 to 60 cm in accordance with another embodiment.

The calculated profiles of the steel surface are then compared with the surface profile data, previously obtained without the tiles, where the data overlap. FIG. 8C shows the steel surface profiles calculated from the lift-off distance data shown in FIG. 8B. More particularly, FIG. 8C illustrates the profile of steel surface under the first scanned region. The light-dotted and solid lines are profiles obtained with and without local demagnetization, respectively. The dashed line shows the actual profile of the surface where the topology data are available from 0 to 60 cm.

The vertical shift in the laser-profiler data is cancelled by shifting the origin of the plot to the starting point of the scans. The dashed curve in the plot represents previously obtained topology data. It is to be noted that the profile obtained with the local demagnetization, i.e., the solid curve, matches the actual profile better than the profile obtained when the demagnetization functionality was turned off, i.e., the dotted curve. The effect is most significant at the beginning of the scans. The same effect is previously observed in lab tests. Deviations of profiles, which were obtained without demagnetization, from actual profiles, were the largest near the scan starting points, yet remained close to 1 mm. These observations suggest that the local demagnetization feature is necessary for better than 1 mm precision, especially for separated-point measurements and short scans.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A pulsed eddy current sensor for measurement of a lift-off distance over a surface of a metallic substrate or a metallic surface, the pulsed eddy current sensor comprising:
   a primary excitation coil to which are applied voltage pulses for generating primary magnetic fields, wherein an interaction of the primary magnetic fields with the metallic substrate produces secondary magnetic fields;
   secondary pick-up probes, each of the secondary pick-up probes located at a different vertical distance from the metallic surface, the secondary pick-up probes used for measuring the primary and secondary magnetic fields and for producing a differential signal that is representative of the lift-off distance; and
   an adjustment mechanism for adjusting a distance between the secondary pick-up probes for substantially balancing the secondary pick-up probes.

2. The pulsed eddy current sensor of claim 1, wherein the secondary pick-up probes are provided within the primary excitation coil.

3. The pulsed eddy current sensor of claim 2, wherein the primary excitation coil comprises one or more coaxial excitation coils.

4. The pulsed eddy current sensor of claim 2, wherein the secondary pick-up probes comprise a pair of secondary pick-up coils.

5. The pulsed eddy current sensor of claim 4, wherein one of the secondary pick-up coils is wound in a first direction and the other one of the secondary pick-up coils is wound in a second direction, opposite to the first direction, thereby subtracting a signal induced in the one of the secondary pick-up coils from another signal induced in the other one of the secondary pick-up coils thereby producing the differential signal.

6. The pulsed eddy current sensor of claim 4, wherein both secondary pick-up coils are wound in the same direction, but connected with opposing leads thereby subtracting a signal induced in the one of the secondary pick-up coils from another signal induced in the other one of the secondary pick-up coils thereby producing the differential signal.

7. The pulsed eddy current sensor of claim 2, wherein the secondary pick-up probes are connected separately to a differential amplifier that subtracts a signal induced in the one of the secondary pick-up probes from another signal induced in the other one of the secondary pick-up probes thereby producing the differential signal.

8. The pulsed eddy current sensor of claim 1, further comprising a ferrite core provided within each one of the secondary pick-up probes.

9. A pulsed eddy current sensing system for measurement of a lift-off distance over a surface of a metallic substrate or a metallic surface, the pulsed eddy current sensing system comprising:
   a pulse generator for generating voltage pulses;
   a primary excitation coil to which are applied voltage pulses for generating primary magnetic fields, wherein an interaction of the primary magnetic fields with the metallic substrate produces secondary magnetic fields;
   secondary pick-up probes, each of the secondary pick-up probes located at a different vertical distance from the metallic surface, the secondary pick-up probes used for measuring the primary and secondary magnetic fields and for producing a differential signal that is representative of the lift-off distance; and
   an adjustment mechanism for adjusting a distance between the secondary pick-up probes for substantially balancing the secondary pick-up probes.

10. The pulsed eddy current sensing system of claim 9, further comprising a local degaussing circuit for neutralizing a residual magnetization in the metallic surface.

11. The pulsed eddy current sensing system of claim 9, wherein the secondary pick-up probes are provided within the primary excitation coil.

12. A method for three-dimensional mapping of a metallic surface under a low conductivity coating, a distance from the top of the low conductivity coating to the metallic surface defining a lift-off distance, the method comprising:
- performing a series of measurements of the lift-off distance or depth at reference positions covering two dimensions including latitude and longitude over the low conductivity coating wherein performing a series of measurements comprises:
  - applying voltage pulses onto a primary excitation coil for generating primary magnetic fields, wherein an interaction of the primary magnetic fields with the metallic surface produces secondary magnetic fields;
  - measuring the primary and secondary magnetic fields and producing a differential signal that is representative of the lift-off distance using secondary pick-up probes, each of the secondary pick-up probes being located at a different vertical distance from the metallic surface; and
  - using an adjustment mechanism, adjusting a distance between the secondary pick-up probes for substantially balancing the secondary pick-up probes; and
- integrating the series of measurements with the reference positions to produce a three-dimensional map of the metallic surface under a low conductivity coating.

* * * * *